United States Patent
Kang

(10) Patent No.: US 9,192,445 B2
(45) Date of Patent: Nov. 24, 2015

(54) REGISTRATION AND NAVIGATION USING A THREE-DIMENSIONAL TRACKING SENSOR

(71) Applicant: MAKO Surgical Corp., Fort Lauderdale, FL (US)

(72) Inventor: Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 420 days.

(21) Appl. No.: 13/714,066

(22) Filed: Dec. 13, 2012

(65) Prior Publication Data

US 2014/0171962 A1 Jun. 19, 2014

(51) Int. Cl.
*A61B 19/00* (2006.01)

(52) U.S. Cl.
CPC ............. *A61B 19/20* (2013.01); *A61B 19/5244* (2013.01); *A61B 19/2203* (2013.01); *A61B 2019/505* (2013.01); *A61B 2019/5255* (2013.01); *A61B 2019/5265* (2013.01); *A61B 2019/5268* (2013.01)

(58) Field of Classification Search
CPC ............... A61B 19/20; A61B 19/5244; A61B 2019/505; A61B 19/5255; A61B 2019/5265; A61B 2019/5268
See application file for complete search history.

(56) References Cited

U.S. PATENT DOCUMENTS

| | | |
|---|---|---|
| D616,908 S | 6/2010 | Labak |
| D622,854 S | 8/2010 | Otto et al. |
| 7,799,084 B2 | 9/2010 | Clemow et al. |
| 8,206,053 B2 | 6/2012 | Bennett et al. |
| 8,249,345 B2 | 8/2012 | Wu et al. |
| 2002/0156375 A1* | 10/2002 | Kessman et al. ............... 600/439 |
| 2003/0073901 A1* | 4/2003 | Simon et al. ................... 600/424 |
| 2004/0034283 A1 | 2/2004 | Quaid |
| 2006/0058644 A1 | 3/2006 | Hoppe et al. |
| 2006/0142657 A1* | 6/2006 | Quaid et al. ................... 600/424 |
| 2006/0190086 A1 | 8/2006 | Clemow et al. |
| 2007/0239153 A1* | 10/2007 | Hodorek et al. ................. 606/41 |
| 2008/0208041 A1 | 8/2008 | Gilboa |
| 2008/0262812 A1 | 10/2008 | Arata et al. |
| 2009/0068620 A1 | 3/2009 | Knobel et al. |
| 2009/0306499 A1 | 12/2009 | Van Vorhis et al. |
| 2010/0110165 A1 | 5/2010 | Iizuka |
| 2010/0153076 A1 | 6/2010 | Bellettre et al. |
| 2011/0066079 A1 | 3/2011 | Otto et al. |

(Continued)

FOREIGN PATENT DOCUMENTS

| | | | |
|---|---|---|---|
| EP | 2 436 333 A1 | 4/2012 | |
| WO | WO-2006/091494 A1 | 8/2006 | |

OTHER PUBLICATIONS

U.S. Appl. No. 13/562,163, filed Jul. 30, 2012, Kang, et al.

(Continued)

*Primary Examiner* — Huy T Nguyen
(74) *Attorney, Agent, or Firm* — Foley & Lardner LLP

(57) ABSTRACT

Systems and methods for registration and navigation using a 3D tracking sensor are shown and described. The systems and methods utilize a 3D tracking sensor coupled to a portable surgical element to track a trackable element fixed to an object. The pose of the trackable element is determined based at least in part on information provided by the 3D tracking sensor, and the object is registered to a three-dimensional representation of the object. The 3D tracking sensor can also be used to track various objects during a surgical procedure.

22 Claims, 6 Drawing Sheets

(56) References Cited

U.S. PATENT DOCUMENTS

| | | | |
|---|---|---|---|
| 2011/0082462 A1 | 4/2011 | Suarez et al. | |
| 2012/0029387 A1* | 2/2012 | Wei et al. | 600/587 |
| 2012/0143049 A1 | 6/2012 | Neubauer et al. | |
| 2013/0169423 A1 | 7/2013 | Iorgulescu et al. | |
| 2013/0172905 A1 | 7/2013 | Iorgulescu et al. | |
| 2013/0173008 A1 | 7/2013 | Bechtold et al. | |
| 2014/0225999 A1 | 8/2014 | Bracke et al. | |

OTHER PUBLICATIONS

International Search Report and Written Opinion for PCT Application No. PCT/US/2013/074373 dated Mar. 6, 2014, 14 pages.

* cited by examiner

REGISTRATION AND NAVIGATION USING A THREE-DIMENSIONAL TRACKING SENSOR

BACKGROUND

The present invention relates generally to the fields of registration and navigation of objects, and more particularly to registration and navigation using a three-dimensional tracking sensor.

Three-dimensional tracking sensors ("3D tracking sensors") enable tracking of the position and orientation (i.e., pose) of a moving object. For example, the KINECT 3D tracking sensor for WINDOWS employs a camera and infrared depth sensor to enable skeletal and facial tracking 3D tracking sensors have been implemented, for example, in the gaming industry (e.g., the KINECT tracking sensor for the XBOX 360 gaming system) to allow users to interact with a computer or other device without physically touching the device.

Another example of a 3D tracking sensor is the 3D tracking sensor developed by Leap Motion, Inc. (San Francisco, Calif.). The device developed by Leap Motion, Inc. is capable of tracking objects located in a 3D "interaction space" around the device. By moving objects (e.g., a hand) within the interaction space, a user can interact with and control software communicably linked to the device. For example, a user might connect the device to a laptop computer, and without physically touching a mouse or laptop screen, click and scroll by performing gestures in 3D space.

Another example of a 3D tracking sensor is disclosed in U.S. Patent Publication No. 2010/0110165, which is hereby incorporated by reference in its entirety. U.S. Patent Publication No. 2010/0110165 discloses systems and methods for obtaining and calculating three-dimensional information related to one or more target objects.

SUMMARY

One embodiment of the invention relates to a surgical system. The surgical system includes a 3D tracking sensor coupled to a portable surgical element and a trackable element fixed to an object. The surgical system further includes a surgical controller to determine a pose of the trackable element based at least in part on information provided by the 3D tracking sensor and register the object to a three-dimensional representation of the object.

Another embodiment of the invention relates to a method for registration using a 3D tracking sensor. The method includes tracking a trackable element using a 3D tracking sensor, wherein the 3D tracking sensor is coupled to a portable surgical element and the trackable element is fixed to an object; determining a pose of the trackable element based the information provided by the 3D tracking sensor; and registering the object to a three-dimensional representation of the object.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

The exemplary embodiments described herein relate to surgical applications using a 3D tracking sensor, such as the device developed by Leap Motion, Inc. (described above), capable of tracking the pose of an object relative to the 3D tracking sensor. Two exemplary applications utilizing a 3D tracking sensor are registration and navigation during a surgical procedure. According to one embodiment, the 3D tracking sensor is used to register an object, such as a portion of a patient's anatomy, to a three-dimensional representation of the patient's anatomy created prior to the surgical procedure. In another embodiment, the 3D tracking sensor is used to facilitate tracking of objects (e.g., the patient, surgical tools) during a surgical procedure.

Figure 1:
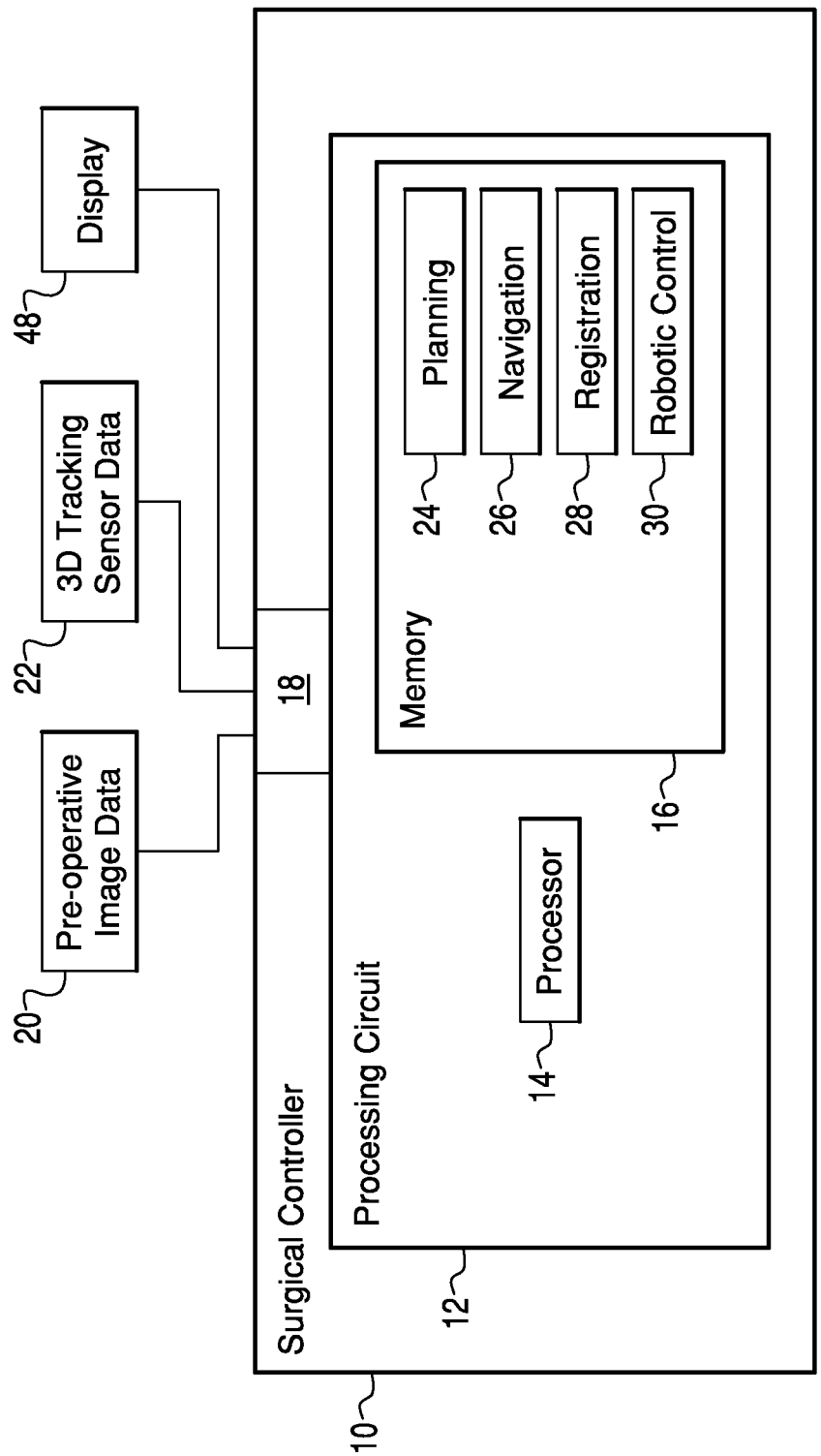
FIG. 1 is a block diagram of a surgical controller, according to an exemplary embodiment.

Referring to FIG. 1, a surgical controller 10 can be utilized to implement the various functions (e.g., calculations, control mechanisms, processes) described herein. Surgical controller 10 includes a processing circuit 12 having a processor 14 and memory 16. Processor 14 can be implemented as a general purpose processor, an application specific integrated circuit (ASIC), one or more field programmable gate arrays (FPGAs), a group of processing components, or other suitable electronic processing components. Memory 16 (e.g., memory, memory unit, storage device, etc.) is one or more devices (e.g., RAM, ROM, Flash-memory, hard disk storage, etc.) for storing data and/or computer code for completing or facilitating the various processes described in the present application. Memory 16 may be or include volatile memory or non-volatile memory. Memory 16 may include database components, object code components, script components, or any other type of information structure for supporting the various activities described in the present application. According to an exemplary embodiment, memory 16 is communicably connected to processor 14 and includes computer code for executing one or more processes described herein. The memory 16 may contain a variety of modules, each capable of storing data and/or computer code related to specific types of functions. In one embodiment, memory 16 contains several modules related to surgical procedures, such as a planning module 24, a navigation module 26, a registration module 28, and a robotic control module 30.

It should be understood that the surgical controller 10 need not be contained in a single housing. Rather, components of the surgical controller 10 may be located in various locations of the surgical system 100 depicted in FIG. 2, or even in a remote location. Components of surgical controller 10 may be located, for example, in a 3D tracking sensor 36 or in a haptic device 32.

The present disclosure contemplates methods, systems and program products on any machine-readable media for accomplishing various operations. The machine-readable media may be part of or may interface with the surgical controller 10. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Referring again to FIG. 1, the surgical controller 10 further includes a communication interface 18. The communication interface 18 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). For example, communication interface 18 can include an Ethernet card and port for sending and receiving data via an Ethernet-based communications link or network. In another example, communication interface 18 can include a WiFi transceiver for communication via a wireless communications network. Thus, if the surgical controller 10 is physically separate from other components of the surgical system 100 shown in FIG. 2, such as the 3D tracking sensor 36 and the haptic device 32, the communication interface 18 can enable wireless communications between the surgical controller 10 and these separate components.

Prior to a surgical procedure, pre-operative image data 20 of any form (e.g., two-dimensional images, a three-dimensional model) may be transmitted to the surgical controller 10 via the communication interface 18. The pre-operative image data 20 can then be utilized during the development of a surgical plan. To obtain the pre-operative image data 20, a patient may be scanned using any known imaging technique, such as CT, MRI, or ultrasound. The scan data is then segmented (either by the surgical controller 10 or by another processor) to obtain a three-dimensional representation of a portion of the patient's anatomy. For example, prior to a surgical procedure on the knee, three-dimensional representations of the patient's femur and tibia are created. In another embodiment, a three-dimensional representation may be obtained by selecting a three-dimensional model from a database or library of bone models. The selected bone model(s) from the database can then be deformed based on specific patient characteristics to obtain a three-dimensional representation of a portion of the patient's anatomy.

The planning module 24, located in memory 16 of the surgical controller 10, can store the instructions necessary to process the incoming pre-operative image data 20 and to utilize the image data 20 during surgical planning Once the three-dimensional representation of a portion of the patient's anatomy has been created, a surgeon can develop a surgical plan based on the three-dimensional representation. The surgical plan can include the desired modifications to bone (e.g., holes, cuts) to be created during the surgical procedure, and can further include the desired placement for any components to be implanted during the surgical procedure. As one example, prior to a surgical procedure to replace one or more articular surfaces of the knee with an implant, a surgical plan might be created to model the planned bone removal and placement of the implant.

The surgical plan may further include haptic objects. During a surgical procedure, the haptic objects interact with a surgical tool 34 coupled to a haptic device 32 (FIG. 2) to control movement of the surgical tool 34, as described in U.S. Pat. No. 8,010,180, titled "Haptic Guidance System and Method," granted Aug. 30, 2011, and hereby incorporated by reference herein in its entirety. In various embodiments, a haptic object may represent a desired trajectory of the surgical tool 34, a desired modification to the bone (e.g., the bounds of a hole or cut), or a three-dimensional portion of bone to be removed by the surgical tool 34. The haptic device 32 is used in an interactive manner by a surgeon, and the haptic objects control (e.g., guide or constrain) movement of the surgical tool 34 to assist the surgeon during the surgical procedure. The robotic control module 10 (FIG. 1) within the surgical controller 10 can store the instructions necessary to haptically control the surgical tool 34.

Prior to utilizing the haptic device 32 during a surgical procedure, the patient's anatomy must be registered to the three-dimensional representation of the patient's anatomy. Registration processes involve correlating the coordinate system of the patient's actual anatomy (in physical space) to the coordinate system of the three-dimensional representation of the patient's anatomy (in virtual space). Once registered to the virtual representation, the pose of the patient's anatomy can be tracked in real-time during the surgical procedure, as described further below. Tracking the patient's anatomy, as well as the location of surgical tool 34, is necessary to enable haptic control of the surgical tool 34 (and thus implementation of the surgical plan).

During certain methods of registration, such as the point-based registration method described in U.S. Pat. No. 8,010,180, the portion of the patient's anatomy to be registered is tracked by a navigation system during the registration process. For example, during registration of a bone, a navigation system tracks a trackable element fixed to the bone. Navigation systems typically include a camera that is fixed relative to the coordinate system of the operating room. In these navigation methods, the fixed camera detects the trackable element fixed to the movable object to be tracked (e.g., bone). Once the object has been registered, the pose of the object can be calculated based on the trackable element's position, unique geometry, and known geometric relationship to the tracked object.

Figure 2:
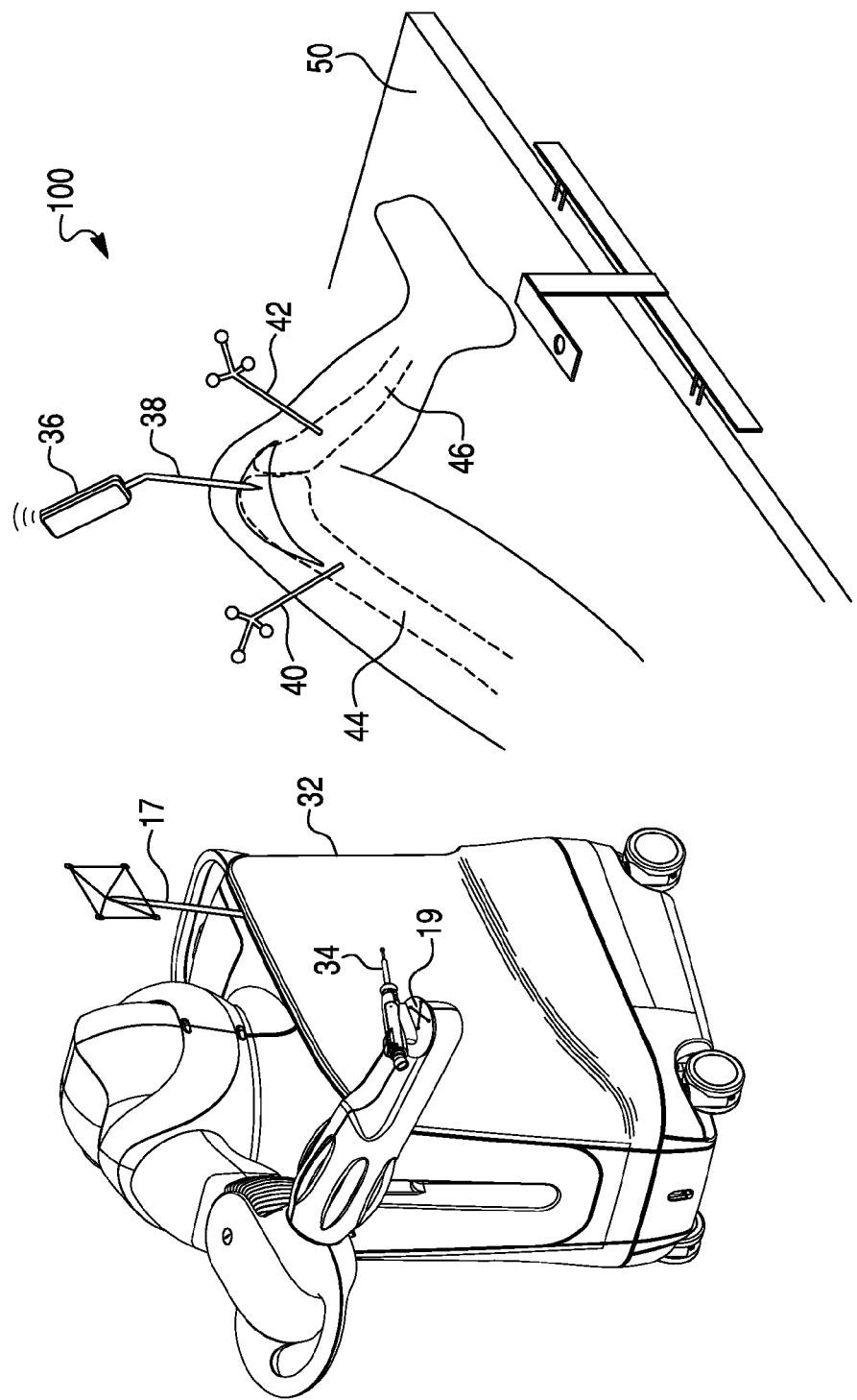
FIG. 2 is a surgical system using a 3D tracking sensor for registration, according to an exemplary embodiment.
Figure 3:
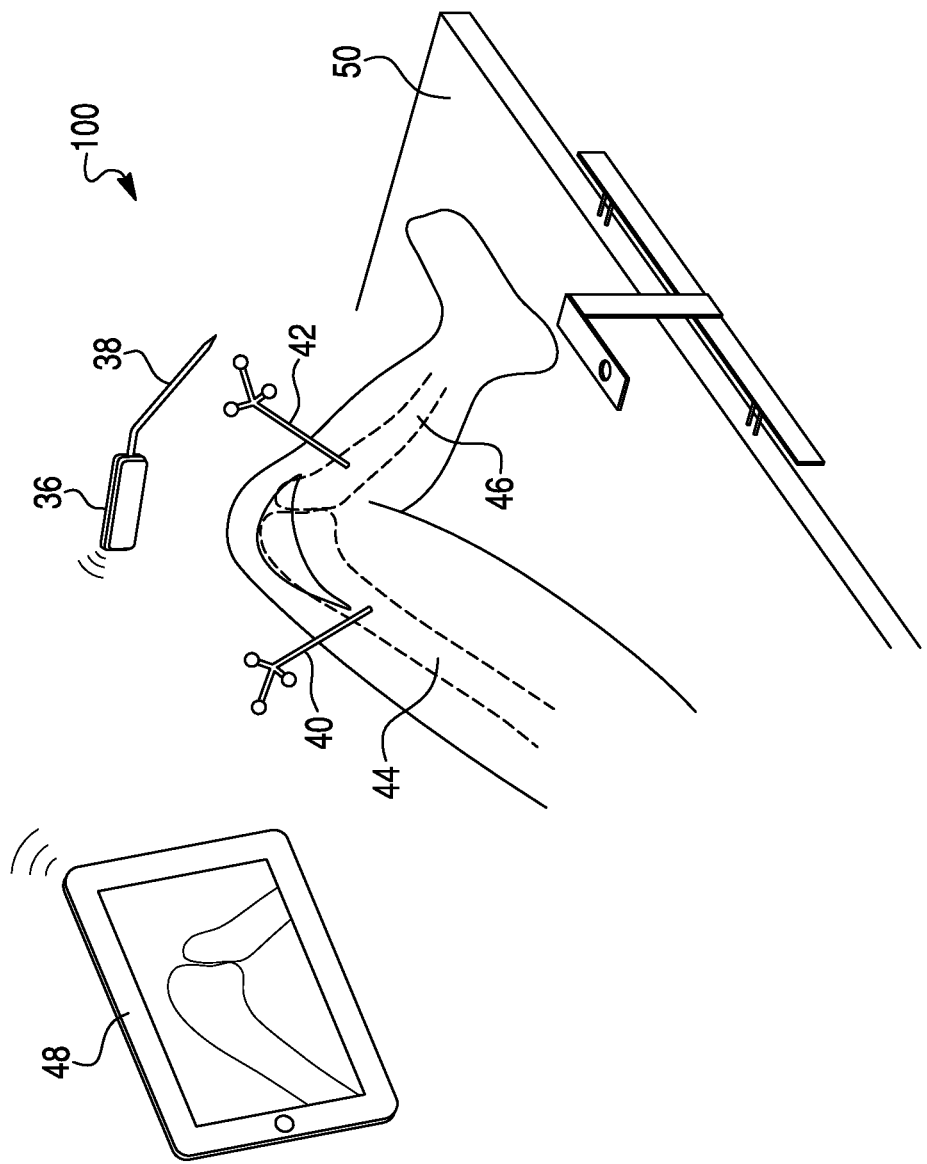
FIG. 3 is a surgical system using a 3D tracking sensor for registration, according to an additional exemplary embodiment.

According to the methods of registration shown in FIGS. 2 and 3, registration of an object is accomplished using a 3D tracking sensor 36. In contrast to other methods of registration, the methods described herein do not require utilization of a navigation system having a camera fixed relative to the operating room to track the object to be registered. Rather, the 3D tracking sensor 36 is coupled to a portable surgical element. The portable surgical element can be any surgical element or object that is or can be repositioned during a surgical procedure without affecting the ability of the 3D tracking sensor to perform its intended functions. Examples of portable surgical elements include a registration probe, a surgical tool, a haptic device, or a portion of a patient's anatomy (e.g., bone). Referring again to FIG. 1, the 3D tracking sensor 36 is capable of communicating wirelessly with the surgical controller 10, and can send 3D tracking sensor data 22 to the surgical controller 10. The instructions to carry out the functions related to tracking as described herein can be stored within navigation module 26 of the surgical controller 10. Similarly, the instructions to carry out the functions related to registration of an object can be stored within registration module 28 of the surgical controller 10.

Referring to FIG. 2, in one embodiment of registration using 3D tracking sensor 36, the 3D tracking sensor 36 is coupled to probe 38. Thus, the relationship between the coordinate system of 3D tracking sensor 36 and the coordinate system of probe 38 is known. A trackable element 40 is placed on the object, such as a bone 44, to be registered. The trackable element 40 can be an array having a recognizable shape that conveys the orientation of the trackable element 40. The probe 38 is then positioned on the bone 44 such that the trackable element 40 is within the interaction space of the 3D tracking sensor 36. The 3D tracking sensor 36 can therefore "see" the trackable element 40, and the pose of the trackable element 40 relative to the 3D tracking sensor 36 can be calculated. Accordingly, the transformation between the coordinate system of the probe 38 and the trackable element 40 can be calculated. In this manner, the surgical controller 10 is able to determine where the tip of registration probe 38 is located relative to the trackable element 40.

Registration of bone 44 can then be accomplished by using the tip of registration probe 38 to contact several points on the bone 44. In one embodiment, the surgeon contacts the bone 44 with the probe 38 fifteen to twenty times. A point cloud is created using the numerous points of contact. The point cloud can then be aligned with the three-dimensional representation of bone 44, which was created preoperatively, to register the bone 44 to the three-dimensional representation.

Referring to FIG. 3, in another embodiment of registration using a 3D tracking sensor 36, the probe 38 is not used to contact points on a bone 44. Instead, the 3D tracking sensor 36 is held such that the trackable element 40 and at least a portion of the surface of bone 44 is within the interaction space of the 3D tracking sensor 36. A point cloud comprising numerous points on the bone 44 is then generated, without having to use the probe 38 to physically contact the bone 44. This point cloud is then aligned with the three-dimensional representation of bone 44 to register the bone 44. An additional trackable element 42 and a portion of another bone 46 may also be within the interaction space, in which case bone 46 can be registered in the same manner as bone 44.

In the embodiment of FIG. 3, a CT scan may be used to create the three-dimensional representation of the bone 44 and/or bone 46 if the 3D tracking device 36 is able to capture enough exposed bone during registration. Alternatively, an MRI could be used to create the three-dimensional representation. A three-dimensional representation showing soft tissue surrounding the bones 44, 46 may be useful if portions of bone exposed to 3D tracking sensor 36 during registration are covered by cartilage or other soft tissue.

Following registration of bone 44, an image of the bone 44 may be output to a display 48, such as a tablet device (FIG. 3) or a standard computer monitor. If physically separate from the display 48, the surgical controller 10 (FIG. 1) can communicate with the display 48 via the communication interface 18. In one embodiment, the display 48 shows a digitally reconstructed radiograph (DRR) of the bone 44 from the perspective of the 3D tracking sensor 36. In this embodiment, the surgeon can manipulate 3D tracking sensor 36 around the patient's anatomy to view a DRR of the anatomy from varying perspectives.

Figure 4:
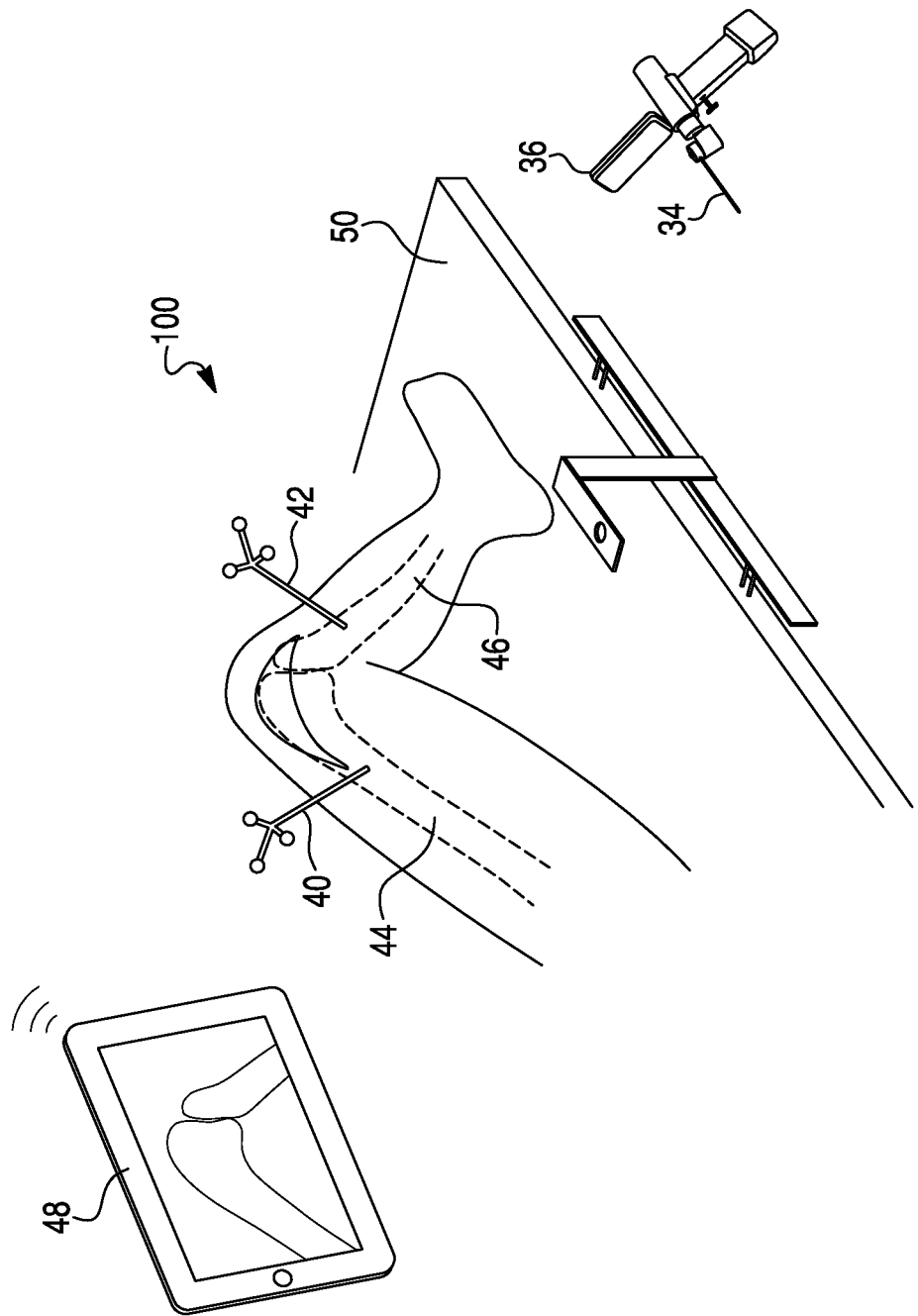
FIG. 4 is a surgical system using a 3D tracking sensor for navigation, according to an exemplary embodiment.

Referring to FIG. 4, in an exemplary embodiment, the 3D tracking sensor 36 is coupled to surgical tool 34 to determine the pose of one or more trackable elements or other objects during a surgical procedure. As in the embodiments of FIGS. 2 and 3, trackable elements 40, 42 are fixed to bones 44, 46, respectively. In one embodiment, the surgical tool 34 is coupled to a haptic device 32, as shown in FIG. 2. As a user repositions the surgical tool 34 during a surgical procedure, the trackable elements 40, 42 remain within the interaction space of the 3D tracking sensor 36. The surgical controller 10 is able to determine the pose of one or more of the trackable elements 40, 42 during the surgical procedure based at least in part on information received from the 3D tracking sensor 36. The 3D tracking sensor therefore tracks the trackable elements 40, 42. If the bones 44, 46 have already been registered, the surgical system 100 also tracks the bones 44, 46 during the surgical procedure (by continuously determining the pose of the trackable elements 40, 42). Thus, during a surgical procedure, the 3D tracking sensor 36 coupled to the surgical tool 34 enables the surgical system 100 to track a variety of objects (e.g., trackable elements, a portion of a patient's anatomy). Furthermore, unlike other navigation systems that require a camera fixed relative to the operating room, the 3D tracking sensor 36 can be freely repositioned without disrupting the surgical system's ability to track objects.

Figure 5:
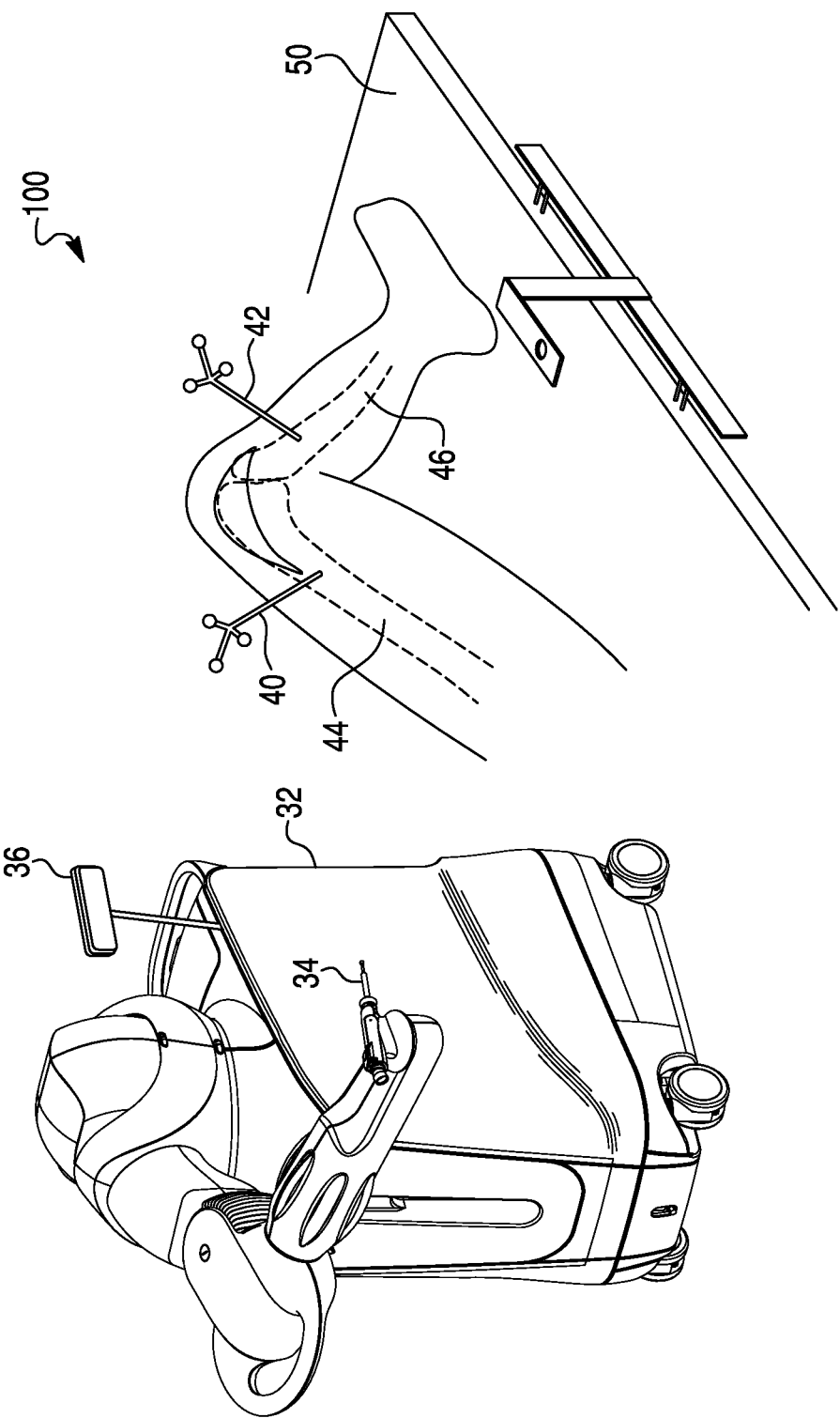
FIG. 5 is a surgical system using a 3D tracking sensor for navigation, according to another exemplary embodiment.

Referring to the exemplary embodiment shown in FIG. 5, the 3D tracking sensor 36 is coupled to the portable haptic device 32. The trackable elements 40, 42 are within the interaction space of the 3D tracking sensor 36. Because each of the trackable elements are within the interaction space of 3D tracking sensor 36, the pose of each of the tracked objects relative to the sensor 36 can be determined by the surgical controller 10. The 3D tracking sensor 36 can therefore be used to determine the pose of bones 44, 46 and any other tracked objects within the surgical system 100. During a surgical procedure, the 3D tracking sensor 36 may be fixed relative to the base of the haptic device 32 such that the coordinate transformation between the base and the 3D tracking sensor 36 is known. The surgical controller 10 can then compute the location of surgical tool 34 based on its position and/or orientation relative to the base of the haptic device 32. The 3D tracking sensor may be mounted to an arm (as shown in FIG. 5) or directly to the haptic device 32. The arm may be adjustable so that a user can position the 3D tracking sensor to ensure that any objects to be tracked are within the interaction space of the 3D tracking sensor 36.

Figure 6:
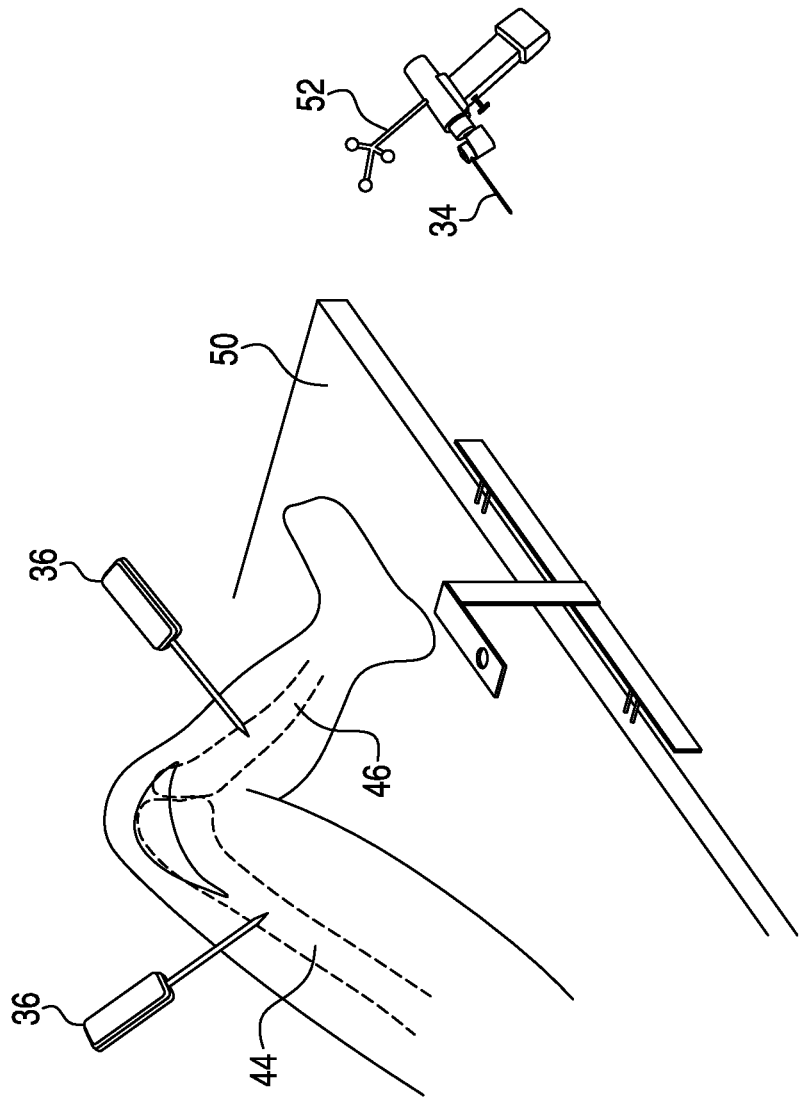
FIG. 6 is a surgical system using multiple 3D tracking sensors for navigation, according to an exemplary embodiment.

Referring to FIG. 6, in another exemplary embodiment, 3D tracking sensors 36 are placed on the patient's bones 44, 46, and a trackable element 52 is fixed relative to the surgical tool 34. The pose of the trackable element 52, and therefore of the surgical tool 34, can therefore be determined based at least in part on information provided by one or more of the tracking sensors 36. Other objects may also be tracked using the 3D tracking sensors 36 coupled to the patient's anatomy.

The construction and arrangement of the systems and methods as shown in the various exemplary embodiments are illustrative only. Although only a few embodiments have been described in detail in this disclosure, many modifications are possible (e.g., variations in sizes, components, and structures of the various elements, values of parameters, mounting arrangements, use of materials, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

Although a specific order of method steps may be described, the order of the steps may differ from what is described. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A surgical system, comprising:
    a 3D tracking sensor coupled to a portable surgical element;
    a trackable element fixed to an object;
    a surgical controller configured to:
        determine a pose of the trackable element based at least in part on information provided by the 3D tracking sensor; and
        register the object to a three-dimensional representation of the object;
    wherein the 3D tracking sensor is configured to obtain three-dimensional information related to the trackable element by capturing at least a first image and a second image of the trackable element; and
    wherein the surgical controller determines the pose of the trackable element at least in part by comparing the image intensities of the first and second images.

2. The surgical system of claim 1, wherein the 3D tracking sensor is configured to communicate wirelessly with the surgical controller.

3. The surgical system of claim 1, wherein the trackable element is an array having a shape configured to convey an orientation of the trackable element.

4. The surgical system of claim 1, wherein the surgical controller is further configured to determine the pose of the object during a surgical procedure based at least in part on information provided by the 3D tracking sensor.

5. The surgical system of claim 1, further comprising a haptic device, wherein the surgical controller is configured to control the haptic device.

6. The surgical system of claim 1, wherein the portable surgical element is a registration probe.

7. The surgical system of claim 6, wherein the surgical controller is configured to register the object using a point cloud, wherein the point cloud includes a plurality of contact points between the registration probe and the object.

8. The surgical system of claim 1, wherein the surgical controller is configured to register the object using a point cloud obtained from the 3D tracking sensor.

9. The surgical system of claim 1, further comprising a display, wherein the surgical controller causes the display to show an image of the object based on a pose of the 3D tracking sensor relative to the object.

10. The surgical system of claim 1, wherein the portable surgical element is a haptic device or a surgical tool.

11. The surgical system of claim 1, wherein the object is a portion of a patient's anatomy.

12. A method for registration using a 3D tracking sensor, comprising:
    tracking a trackable element using a 3D tracking sensor, wherein the 3D tracking sensor is coupled to a portable surgical element and the trackable element is fixed to an object;
    determining a pose of the trackable element based at least in part on information provided by the 3D tracking sensor;
    wherein the 3D tracking sensor tracks the trackable element by capturing at least a first image and a second image of the trackable element;
    wherein the pose of the trackable element is determined at least in part by comparing the image intensities of the first and second images; and
    registering the object to a three-dimensional representation of the object.

13. The method of claim 12, wherein the 3D tracking sensor is configured to communicate wirelessly with a surgical controller.

14. The method of claim 12, wherein the trackable element is an array having a shape configured to convey an orientation of the trackable element.

15. The method of claim 12, further comprising tracking the object using the 3D tracking sensor during a surgical procedure.

16. The method of claim 15, further comprising controlling a haptic device to guide or constrain movement of a surgical tool coupled to the haptic device.

17. The method of claim 12, wherein the portable surgical element is a registration probe.

18. The method of claim 17, wherein the step of registering the object includes contacting the registration probe to the object to obtain a plurality of contact points.

19. The method of claim 12, wherein the step of registering the object includes obtaining information related to the object using the 3D tracking sensor.

20. The method of claim 12, further comprising:
    manipulating the pose of the 3D tracking sensor relative to the object to view a corresponding image of the object on a display.

21. The method of claim 12, wherein the portable surgical element is a haptic device or a surgical tool.

22. The method of claim 12, wherein the object is a portion of a patient's anatomy.

* * * * *